United States Patent [19]

Skoda et al.

[11] 4,172,013

[45] Oct. 23, 1979

[54] PROCESS FOR THE MASS GROWTH OF CELLS AND SYSTEM OF CHAMBERS FOR THE CARRYING OUT THEREOF

[75] Inventors: Rastislav Skoda, Laupheim; Valdemar Pakos, Hüttisheim, both of Fed. Rep. of Germany

[73] Assignee: Dr. Rentschler Arzneimittel GmbH & Co., Fed. Rep. of Germany

[21] Appl. No.: 801,056

[22] Filed: May 27, 1977

[30] Foreign Application Priority Data

May 28, 1976 [DE] Fed. Rep. of Germany ....... 2624047

[51] Int. Cl.$^2$ ................................................. C12K 9/00
[52] U.S. Cl. .................................. 435/240; 435/285; 435/310
[58] Field of Search ................. 195/1.7, 1.8, 127, 139

[56] References Cited

U.S. PATENT DOCUMENTS

| 2,865,816 | 12/1958 | Stefanye et al. | 195/139 |
| 3,062,724 | 11/1962 | Reusser | 195/127 |
| 3,102,082 | 8/1963 | Brewer | 195/139 |
| 3,839,155 | 10/1974 | McAleer et al. | 195/127 |
| 3,843,454 | 10/1974 | Weiss | 195/127 |
| 3,873,423 | 3/1975 | Munder et al. | 195/127 |
| 3,933,585 | 1/1976 | McAleer et al. | 195/1.8 X |

Primary Examiner—Thomas G. Wiseman
Attorney, Agent, or Firm—Gordon W. Hueschen

[57] ABSTRACT

An apparatus for the mass growth of cells, characterized by a plurality of flat troughs which form a stack, seated in an airtight and liquid-tight manner on each other at their free outer edges, wherein, in two corners of each trough, there are provided two overflows which are arranged spaced above the bottom of the trough and open toward the next lower trough, and wherein the overflows of the different troughs are at least approximately aligned, and wherein the overflows of the uppermost and lowermost troughs can be closed, the individual troughs being connected with each other, and a method for the mass growth of diploid cells utilizing the same, are disclosed.

8 Claims, 3 Drawing Figures

PROCESS FOR THE MASS GROWTH OF CELLS AND SYSTEM OF CHAMBERS FOR THE CARRYING OUT THEREOF

Normal diploid cells are required for many purposes, for instance for the production of vaccines and cell products, for human use and for research purposes. Heteroploid cells cannot be used for such purposes since they are carcinogenic, although their growth would be substantially easier.

Normal diploid cells grow only on cell-receptive surfaces, to which they adhere firmly and form a closed, dense, cell layer (monolayer). This permits, on the one hand, a rapid change of the medium without centrifuging the cells off, but, on the other hand, only a given quantity of cells which is dependent on the size of the surface is produced. For multiplication, the cells are dissolved from the surface by means of proteolytic enzymes, such as for instance trypsin or in combination with EDTA. Prepared in a culture flask, the cells adhere within three hours and reach the specific form typical for them in about eight hours. Depending on the density of the preparation and the rate of growth (cell division), the dense cell layer is formed in one to several days. As soon as the cells have reached a given density per square centimeter, which is dependent on the cell strain, they stop multiplying. The principle of the growth of cells on the surface of a substance therefore establishes a natural limit for production in a single unit.

Although theoretically a flat surface could amount to up to $100 \times 100$ cm (1 m$^2$), a practical solution in this manner appears impossible since sterility and frequently also a closed atmosphere must be assured, for which reason only shallow bottles, so called Roux dishes, enter into consideration for all practical purposes; enlarging them to so-called penicillin dishes however resulted in only a two to three times greater area (Roux dishes of glass or of plastic: 100–200 cm$^2$; penicillin dishes: 600 cm$^2$).

The Roux dishes were taken over for the culture of cells from bacteriology, where they had been introduced 100 years ago, it not having been possible to replace them by anything better up to the present time.

For several years it has been attempted to find a practical solution for the problem of enlarging the inner surface of a vessel, and the following possibilities have been proposed for this:

(a) Curving the surface into the shape of a tube which is continuously rotated, so that while the cells grow on the entire inner surface, they are covered with nutrient medium only in the lower one-fifth to one-third. Several systems of these so-called roller tubes are known in which the surface of a vessel has been increased to 500 to 1300 cm$^2$. By arranging up to 100s of tubes in levels one above the other, production units of up to 7200 roller flasks have been produced. The disadvantage of such systems is that each tube is a single unit which must be handled separately, which is very expensive from a technical standpoint. Automation has failed up to the present time in actual practice.

(b) It has been proposed to enlarge the surface of a tube by inserting a worm of cell-receptive plastic material, (W. House, Bulk Culture of Cell Monolayers, pages 338 to 344), which led to the development of a 2 to 20 liter flask of 8,000–80,000 cm$^2$. In accordance with this system, 5 to 10 cell multiplications are said to be obtained, which however has not been confirmed in actual practice, since the cells grow very sparsely on the inner turns of the worm. In this case also there is the disadvantage that each tube represents a unit which must be handled separately, which is very expensive from a technical standpoint. In addition to a relatively high price per vessel, automation has encountered great difficulties in actual practice in the case of this system also.

(c) Another proposal was to increase the surface in a vessel by inserting multi-layer stacks of plates of glass, metal, or plastic. A system proposed by Weiss and Schleicher (1968) consists of a plurality of plates of window glass, spaced 6 mm apart, inserted in tanks of 1 to 200 liters. Similar models of titanium have been placed on the market in two sizes (18,000 and 72,000 cm$^2$) by the New Brunswick Scientifics Company (NBS).

In the head plate of the aforementioned model, there are connections for gasification, change of medium, etc. The cell growth takes place in horizontal or vertical position of the plates, with or without rolling the entire vessel.

One disadvantage of these systems is that a large amount of medium as compared with the surface is required.

(d) It has furthermore been proposed to enlarge the surface in a vessel by the inserting of glass beads (Gey, 1933, Robineaux, 1970; Rudiger, 1975) or Sephadex spheres (van Wezel, Growth of Cell Strains and Primary Cells in Microcarriers in homogenous culture, 1967, page 216; Horug et al., 1974) into the medium within the vessel. There are vessels of 1 to 3 liters, which, in the former case, are operated as quiescent monolayer culture and, in the latter case, as suspension culture. In both cases possibilities are incorporated for the measuring and adjusting of the environmental conditions, for instance $CO_2$, $O_2$, temperature, pH, glucose, etc.

The disadvantage of these systems resides in the necessity of using large quantities of medium in proportion to the cells, and the difficulty of recovering the cells.

(e) A completely new method for the mass growth of cells is the so-called "Hollow Fiber Cartridge System" which consists of a bundle of capillaries of cell-receptive plastic material which is contained within a tube chamber. The cells grow on the outer surface of the capillaries, which are continuously perfused by growth medium. The models now in existence have a surface of about 100 cm$^2$, which is not sufficient for the mass production of cells.

It can be stated that none of the previous systems for the mass growth of cells has reached the stage of routine operational production of cells or of cell products for parenteral administration to humans. From a practical standpoint, a true mass growth of cells has not been obtained with any system, and from a theoretical standpoint all the systems have serious disadvantages, for instance the possibility of microbic and cellular contamination, and the difficulty of rationalization and automation.

A system for the mass growth of cells which is in accord with practical requirements should satisfy the following criteria and is shown in the accompanying figures.

The system should permit a long-lasting cultivation of diploid cells up to the time of their possible transformation, i.e. their transformation as calculated theoretically on basis of the mutation rates of $1:10^6$ to $1:10^{12}$, or of their death, while its special function, for instance the production of interferon, must be retained. In the system, the cells should have minimal exposure to "biohazards", i.e. to the effects of foreign substances and the environment, particularly during the period of harvesting and seeding. The cost of manufacture and production should also be realistic from a financial standpoint.

Figure 1:
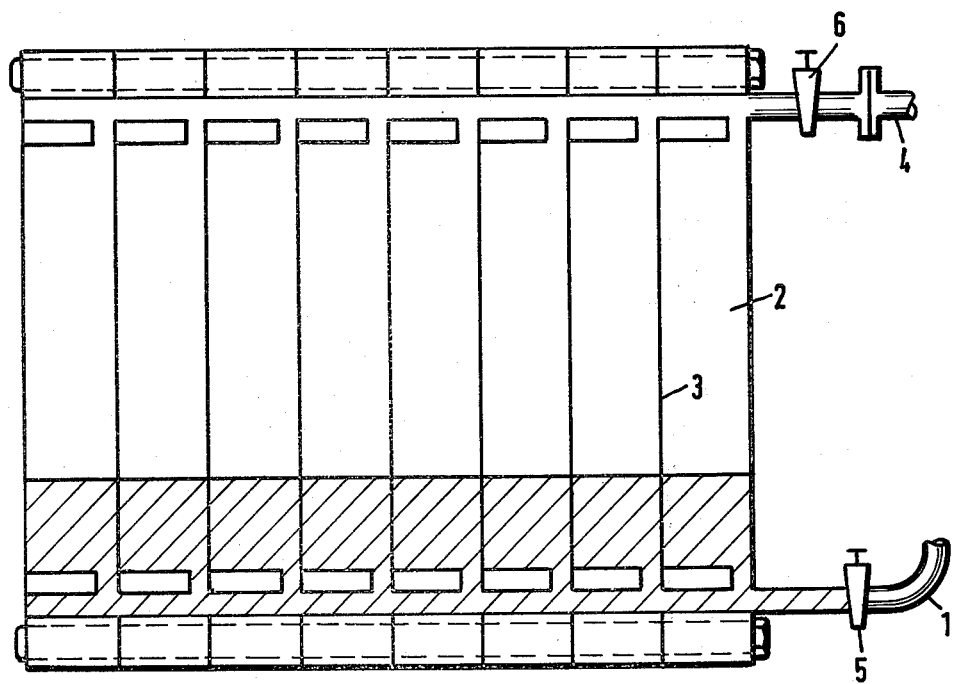
FIG. 1 is a view of the vertical position of the troughs of the cell culture system.
Figure 2:
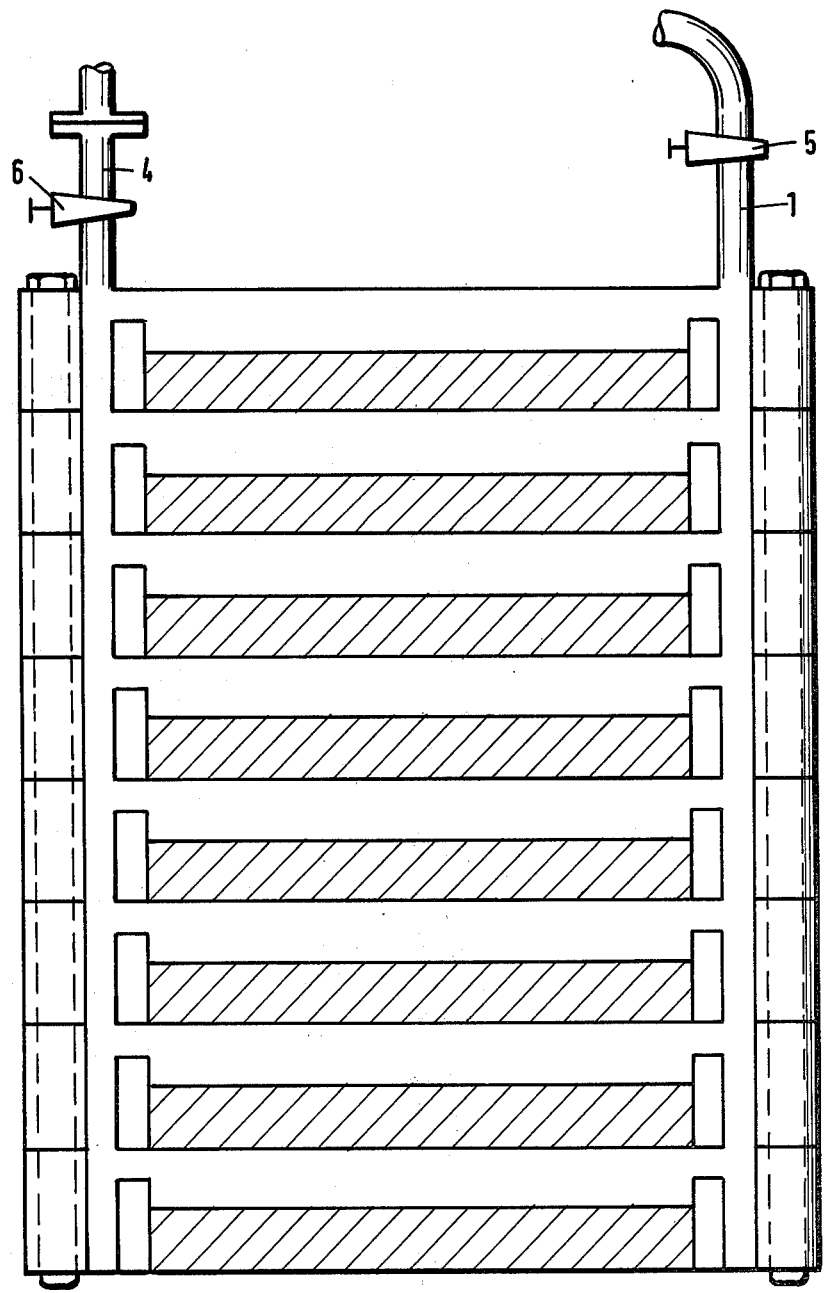
FIG. 2 is a view of the horizontal position of the troughs of the cell culture system.
Figure 3:
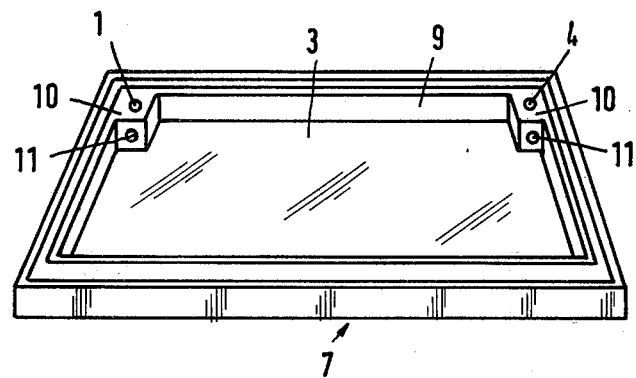
FIG. 3 is a prospective view of individual troughs and a cover plate therefor.
Figure 3:
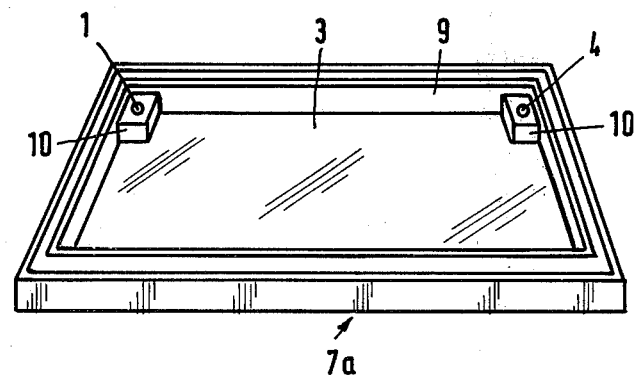
Figure 3:
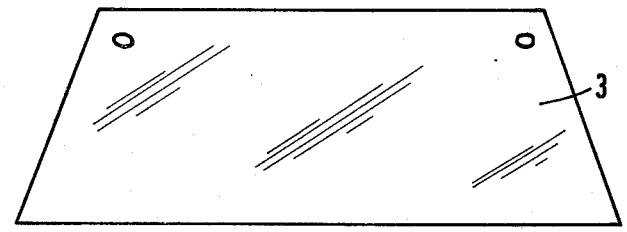

It has now been found that it is possible considerably to increase the useful surface for cell growth and to effect the operations necessary for the growth simultaneously and jointly for several useful surfaces, which permits a substantial rationalization and automation of the growth. The new method is characterized by (a) introducing the nutrient medium, the cell suspension, the trypsin solution or any other liquid components, through a central feed line 1 serving as supply channel into the lower part of a system of communicating chambers 2, which is formed by stacking parallel flat troughs with the bottoms 3 of the troughs arranged substantially vertically (FIG. 1) and allowing it to distribute itself in accordance with the principle of communicating tubes, equalization of the air pressure taking place simultaneously via a central aeration and evacuation channel 4, arranged in the upper part of the chamber system;

(b) after closing the valves 5 and 6 which regulate the feed of the nutrient medium, of the cell suspension, of the trypsin solution, or any other liquid components, and of the air by swinging the chamber system into the horizontal position (FIG. 2), distributing the nutrient medium, etc., over the useful surface of the substantially horizontally arranged troughs;

(c) in the horizontal position, measuring the parameters of the atmosphere prevailing over the medium, correcting them, and effecting the growth of these cells on the useful surfaces of the individual chambers which are now arranged one above the other, in which connection the parameters of the nutrient medium can be controlled and corrected, possibly, by temporarily restoring the chamber system to the vertical position (FIG. 1);

(d) after completion of the cell growth or the production of virus or interferon and the restoring of the chamber system to the vertical position, allowing the detrypsinized cells or the virus or interferon crops to flow out through the central supply channel 1, and (e) working the cells or cell products up in customary manner.

For the carrying out of the method of the invention there is preferably employed an apparatus which will be described below, with reference to the drawings:

The chamber system consists of individual flat troughs whose useful surface may be of various sizes, depending substantially on the technical possibility of their production. The individual troughs have an inner bottom surface 3, which serves as growth or useful surface, and are provided with side walls 9, whose height may amount preferably to 5 to 20 mm. Of course, trough bottoms and walls can also be produced separately and be stacked to form the chamber system in accordance with the invention. In two corners of the short side wall, overflows 10 are provided, which may have the shape of a small tube or square whose height is equal to the short side wall (trough 7) and within the upper part of which there are located one or more openings 11 which serve for the feeding or aerating or exhausting of the chamber in question. The overflows provided may also be shorter than the side walls (trough 7a), as a result of which the necessity of special openings is dispensed with. The height of such shorter overflows is determined by the fact that no liquid may discharge from them in substantially horizontal position (position B) via the central supply or aeration channel.

For example, troughs which are stacked on each other by means of packing rings or glued and held together by means of screws form a stack which may consist of several, for instance 10 to 12, chambers. The overflows of the individual troughs become in the stack, two channels which serve as supply channel 1 and aeration or exhaust channel 4. In the vertical position of the stacks, the supply channel is at the bottom and the air channel at the top. The supply channel advisedly has a multi-way valve at the front inlet, and the aeration channel advisedly has a two-way valve with Millipore ® filter. Both conduits terminate blind at the rear.

The trough can consist of all materials which are suitable for the growth of cells, such as glass, plastic, etc. The troughs preferably consist of polystyrene, the surface of which is treated to make it receptive to the cells.

The feeding of the system of chambers is effected in vertical position by the principle of communicating tubes. The supply channel is connected by hoses to a central supply and evacuation system. The equalization of the air pressure upon the filling and emptying is effected through the ventilation channel.

The filled system of chambers is placed in position B, in which both channels are at the top. In this horizontal incubation position, the medium distributes itself uniformly over the useful surface of the individual chambers. Both channels in this way come into a vertical position; the openings for the individual chambers are then, in horizontal position, close to the top, below the bottom of the next chamber, whereby the coherence of the liquid is interrupted and downward discharge is prevented. In this position aeration, for instance with $CO_2$, is possible.

For emptying, the system of chambers is brought into the vertical position in the manner described, but in reverse direction. For the addition of further substances, the nutrient medium is transferred into the emptying vessel, the desired substances are added there, and the liquid is returned into the chamber system.

In one particularly suitable manner of carrying out the method of the invention, the incubation of the chamber system is effected on a tilting mechanism in order to reduce the amount of nutrient medium and improve the growth of the cells.

A plurality of chamber systems with a common central supply can also be combined on a joint tilting mechanism into a single larger unit and be handled as such. The entire unit can be installed in an incubator.

| Example of the calculation of the cell production | | |
|---|---|---|
|  |  | $1 \text{ cm}^2 = 10^5$ cells |
| 1 trough = 20 × 30 cm | = | $600 \text{ cm}^2 = 6 \times 10^7$ cells |
| 20 troughs = 1 stack | = | $12,000 \text{ cm}^2 = 1.2 \times 10^9$ cells |
| 1 battery = 20 stacks | = | $240,000 \text{ cm}^2 = 2.4 \times 10^{10}$ cells |

| Example of the calculation of the cell production | | | |
|---|---|---|---|
| Consumption of medium | for 1 trough | 1 stack | 1 battery |
| with height of 1 mm | 60 ml | 1,200 | 24,000 ml |
| with height of 2 mm | 120 ml | 2,400 | 48,000 ml |
| with height of 3 mm | 180 ml | 3,600 | 72,000 ml |

The technical advantages of the method of the invention and of the chamber system which serves for the carrying out thereof are, in particular, the following:

1. Due to the enlarging of the surface available for the cell growth and the uniformity of the operating procedures, uniform conditions are assured for the cell growth throughout the entire system of a stack or battery, whereby the theoretical probability of cell transformation by mutation at places of different conditions is reduced.

2. The simple central supply and aeration reduces to a minimum the risk of so-called biohazards, particularly at the time of seeding, multiplication of the cells by microbic or cellular contamination, etc.

3. Environmental factors such as $CO_2$, $O_2$, $N_2$, pH, nutrients, etc., can easily be measured and regulated.

4. Increased sterility is made possible in all operations, so that an addition of antibiotics can be avoided.

5. Very good utilization of the space is possible, i.e. a good ratio between growth surface and space required.

6. Use of cell-receptive plastic material, advisedly polystyrene, in which the cells grow best.

We claim:

1. Method for the mass growth of cells, comprising the steps of:
   (a) introducing a cell suspension, nutrient medium, or other solution related to cell growth and harvesting into a system of communicating chambers which is comprised by a stack of parallel flat troughs having side walls seated in airtight and liquid-tight manner on each other at the outer edges of the side walls and whose bottoms are arranged substantially vertically and, except for the trough bottom most remote from the point of said introduction, are provided with overflow openings in edge areas thereof which provide two substantially continuous channels within said stack at a lower edge area and an upper edge area thereof, when said bottoms are so substantially vertically arranged, the lower edge area channel being connected to a central supply channel and the upper edge area channel being connected to a central aeration and exhaust channel, said introduction being via said central supply channel,
   (b) allowing the same to distribute itself by gravity and by means of said lower edge area channel,
   (c) equalizing the air pressure at the same time via said central aeration and exhaust channel at the upper part of the system,
   (d) closing the central supply and the central aeration or exhaust channels,
   (e) swinging the system of chambers so said trough bottoms are in the horizontal position, thereby distributing the cell suspension, nutrient medium, or other solution over the surface of the substantially horizontal troughs,
   (f) maintaining properties suitable for cell growth in nutrient medium in said troughs and in the atmosphere thereabove and effecting growth of the cells, and
   (g) completing the desired cell growth,
   (h) restoring the system of chambers to the vertical position, and
   (i) recovering the cell growth suspension or cell growth products.

2. Method according to claim 1, including the further steps of measuring and correcting the properties of the medium while said system is in the vertical position, or measuring and correcting the properties of the atmosphere prevailing over the medium while said system is in the horizontal position.

3. Method according to claim 1, wherein the substantially horizontal system of chambers is maintained in movement by tilting during growth of the cells in step (f).

4. System of communicating chambers suitable for the mass growth of diploid cells and for carrying out the method of claim 1 comprising a plurality of parallel flat substantially rectangular troughs which are stacked at the outer edges of their side walls in a fluid and airtight manner, each of which troughs has a principal growth area defined by the bottom and the inner edges of side walls of the trough, and which have channels in two of the edge areas of the side walls which are connected to the growth area openings in the edge areas; the plurality of channels in the stacked troughs forming two continuous internal channels which provide communication between the growth areas of adjacent troughs; the channels and overflow openings of the uppermost and lowermost troughs being adapted to be closed forming a fluid and airtight system of communicating chambers; and when the stack is placed so that the troughs are on their sides, one of the channels being adapted to act as a supply channel for nutrient media while the other acts as an aerator or exhaust channel.

5. Apparatus according to claim 4, wherein the overflows have a height not greater than the height of the said upstanding side walls and have an opening in their upper part.

6. Apparatus according to claim 4, wherein the trough bottoms consist of cell-receptive polystyrene.

7. Apparatus according to claim 4, including also a central supply channel, to which one internal channel is adapted to be connected for supply and emptying, and a central exhaust and aeration channel to which the other internal channel is adapted to be connected for aeration and exhaust.

8. Apparatus of claim 4, wherein the two overflow openings in each of two edge areas of each trough are in each of two corners of each trough.

* * * * *